US006863905B1

United States Patent
Shanbrom

(10) Patent No.: US 6,863,905 B1
(45) Date of Patent: Mar. 8, 2005

(54) ENHANCED IODINE TREATMENT OF DRINKING WATER

(75) Inventor: Edward Shanbrom, Santa Ana, CA (US)

(73) Assignee: Shanbrom Technologies, LLC, Ojai, CA (US)

( * ) Notice: Subject to any disclaimer, the term of this patent is extended or adjusted under 35 U.S.C. 154(b) by 120 days.

(21) Appl. No.: 10/154,105

(22) Filed: May 21, 2002

(51) Int. Cl.[7] .................... A01N 59/12; A01N 37/00; C02F 1/42; C02F 1/76
(52) U.S. Cl. .................. 424/667; 210/660; 210/681; 210/683; 210/753; 210/754; 422/28; 422/30; 422/31; 422/37; 422/139; 422/140; 422/141; 422/142; 514/557; 514/574
(58) Field of Search ................. 210/660, 681, 210/683, 753, 754; 422/28, 30, 31, 37, 139, 140, 141, 142; 424/667, 669; 514/557, 574

(56) References Cited

U.S. PATENT DOCUMENTS 6,045,787 A    4/2000   Shanbrom ................ 424/78.24

Primary Examiner—Michael G. Hartley
Assistant Examiner—Frank Choi
(74) Attorney, Agent, or Firm—Reed Smith

(57) ABSTRACT

A mixed bed of iodine source/iodine capture resin provides high flow rates that are useful for treatment of water. The ratio of source/capture resin can be adjusted to meet the goals of the system. If insufficient iodine is being provided, the source resin amount can be increased relative to the capture resin. If excess iodine or iodide are found in the treated water, the capture resin amount can be increased relative to the source resin. The release of iodine from the source resin and its effectiveness can be significantly enhanced by using a mixed bed system in which one or both of the source and the capture ion exchange resins have had their exchange sites saturated with the anion of an organic acid such as citrate and/or isocitrate. This significantly increases the amount of iodine released into aqueous solution and enhances the disinfecting power of that iodine.

22 Claims, No Drawings

ENHANCED IODINE TREATMENT OF DRINKING WATER

BACKGROUND OF THE INVENTION

1. Area of the Art

The present invention is in the field of treatment of drinking water to destroy water-borne pathogens and is more specifically in the area of treating water with iodine.

2. Description of the Prior Art

Water-borne disease has long been the bane of human civilization. As soon as human population density becomes significant contamination of drinking water becomes a problem. Many bacterial, viral and protozoan pathogens employ a fecal route of distribution. Generally, such pathogens can exist for a considerable—in some cases indefinite—period of time suspended in water. A small amount of infected human waste can contaminate a large volume of water. With steams and rivers the contaminating incident may occur out of sight upstream. With ground water human wastes can diffuse into wells and cause contamination from considerable distance. When an unsuspecting individual drinks such contaminated water without taking steps to destroy the pathogens, a disease state may rapidly ensue—and that person's wastes may spread further contamination.

Water and sewage treatment are major factors in making cities and other large human populations possible. Most of us take the safety of municipal drinking water for granted. However, one has only to spend time in the Third World to learn that there are many large and apparently modern cities where the tap water cannot be safely drunk. Contaminated water can be made safe to drink by any of a number of treatments that destroy pathogens in the water. The simplest treatment is undoubtedly boiling the water. Essentially all water-borne pathogens can be destroyed by a few minutes of exposure to boiling temperatures—at least at sea level. However, it is not practical to boil the water supply for an entire city let alone the water supply for a single home. Therefore, chemical treatments to destroy pathogens have become the leading methods for disinfection of water. Pathogens can be destroyed by reactive chemicals such as halogens. Most municipal water supplies are treated with chlorine, either as the free gas or as a reactive compound such as sodium hypochlorite and chlorine dioxide (or in some cases an organic compound such as Chloramine-T (n-chloro-para-toluene sulfonamide sodium salt)) may be used. Chlorine is a favored disinfecting agent because it has residual activity and continues to kill pathogens as the water flows through the pipes.

Optimal chlorination of water can be fairly complex especially where gaseous chlorine is employed. Consequently there has remained a need for a simpler disinfecting method to use for single wells or for portable use. For such purposes another halogen, iodine, has proven to be effective. While pure iodine is a solid that is only slightly soluble in water (0.3 g/l at 20° C.), solutions of iodine can be made in alcohol or potassium iodide, or water saturated with iodine can be employed. Effective concentrations of iodine can then be metered or injected into water using such a solution. Further, residual iodine is often more palatable than residual chlorine. A potential drawback of iodine is that unless extremely high concentrations of iodine are employed, it may take thirty minutes or more for the iodine to destroy all of the pathogens. Also, the iodine becomes converted into iodide so that iodine disinfected water generally has an appreciable iodide concentration. Iodide is used biologically in the synthesis of thyroid hormone, and the safety of long-term ingestion of water with increased iodide has not been established. Another problems is that iodine is sensitive to the temperature and pH of the water to be disinfected. At low temperatures (below about 10° C.) and/or low pH's iodine disinfection can be very slow.

Recently methods of using iodine bound to ion exchange resins have been developed for water treatment. Using iodine bound to resin simplifies the addition of iodine because a simple flow through cartridge can be provided that combines filters to remove particulates with the iodine dispensing resin. In theory all that is necessary is to control the flow rate of the water to achieve disinfection. It will be appreciated that there is an inverse relationship between flow rate and disinfection. If the flow rate is too high insufficient iodine is liberated from the resin to effect adequate destruction of pathogens. At a low flow rate disinfection may be excellent, but the volume of water produced is insufficient to meet requirements.

A potential advantage of resins is that ion exchange resins can also be used to remove iodide and residual iodine from the treated water. This gives the potential for easily purified water with no iodine or iodide traces. The drawback to this approach is that iodine normally needs to contact the pathogens for several minutes to destroy them. This suggests that a holding tank would be required between the iodine resin and the iodine removal resin. This is especially true because the levels of iodine released from iodinated resin are usually quite low. This greatly complicates the process and increases the size of the purification apparatus.

The present inventor has long been involved in using iodine to disinfect blood and other biological products. The requirements of a biological disinfection system are related to but somewhat different from the requirements for water treatment. In water treatment it is desired to completely kill the pathogens as quickly as possible in as large a volume of water (flow rate) as possible. In the case of water treatment with iodine it is desirable to have as little iodine or iodide as possible in the end product. Volume and speed, per se, are not as important in biological disinfection. It is important, however, to kill all pathogens with as little addition (iodine and iodide) to the final product as possible. Perhaps the most critical thing in biological disinfection is to avoid damaging the biological product undergoing disinfection.

Iodine is an effective disinfectant because it is chemically reactive and chemically damages the pathogens. However, in the case of trying to kill pathogens in blood plasma, the iodine is also capable of reacting with proteins and other biomolecules that comprise the blood plasma. As a result many iodine treatments that completely destroy the pathogens in blood plasma also severely damage critical blood proteins. The present inventor has worked hard to develop systems to kill pathogens while sparing labile proteins and other biomolecules. One approach has been to add iodine and then rapidly remove it (by binding or capture) before the labile proteins are damaged. One of the most successful approaches employed by the present inventor has been to use ion exchange resins to supply iodine and also to remove iodine and iodide. Reference is made to U.S. Pat. No. 6,045,787 to the present inventor. In that patent is disclosed the counterintuitive idea of blending iodine containing and iodine capturing resin in a single column. At the correct flow rate such a mixture does a superior job of disinfecting protein and other solutions without damaging labile biomolecules.

The mixed iodine/capture resins are also effective at disinfecting water. However, with blood plasma and similar biologic products, total treatment volumes are in the neighborhood of one to a few liters. Therefore, flow rates in the region of a few milliliters per minute are adequate. For water treatment flow rates of one to several liters per minute, or greater, are required. Even at high flow rates the mixed resin system of U.S. Pat. No. 6,045,787 is somewhat effective at killing bacteria. Unfortunately, at such high flow rates destruction of some types of virus is not adequate. This problem could be dealt with by constructing a very large column so that contact time of the pathogens with the resin would be significantly increased. This would, however, negate one of the attractive features of a resin based treatment system-compact size.

SUMMARY OF THE INVENTION

I have discovered that a mixed bed of iodine source/iodine capture resin can be adapted to provide high flow rates that are useful for treatment of water. In the typical mixed resin system an iodinated resin (by iodinated I mean resin containing chemically free—that is chemically uncombined—iodine) or an iodinated anion exchange resin (source) is mixed with an anion exchange resin (capture). Iodine is bound to and/or dissolved into the source resin so that aqueous liquid in contact with the source resin dissolves a quantity of iodine. The biological molecules that make up pathogens preferentially take up the iodine. Reaction of the iodine with the pathogens and with any dissolved or suspended organic matter generates iodide ions. The iodide ions are taken up by the ion exchange capture resin that is mixed with the source resin. This is an ion exchange resin which liberates whatever anion (usually chloride) is already bound to the exchange site. At the same time the free iodine becomes reversibly bound to the capture resin. The net effect is that water exiting from the resin column contains little or no iodine or iodide. The exiting water does contain additional chloride or other exchanged anion.

In the mixed bed system, the ratio of source/capture resin can be adjusted to meet the goals of the system. If insufficient iodine is being provided for a particular flow rate, the source resin amount can be increased relative to the capture resin. If excess iodine or iodide are found in the treated water, the capture resin amount can be increased relative to the source resin. Unfortunately, even pure source resin may not release sufficient iodine under typical water treatment conditions. I have discovered that release of iodine from the source resin can be significantly enhanced by using a mixed bed system in which one or both of the source and the capture ion exchange resins have had their exchange sites saturated with the anion of a small organic acid. By "small organic acid" I mean I mean mono, di and tricarboxylic acids or between two and six carbons. At this time the favored organic anions are citrate and/or isocitrate. These anion are only very slowly released from the resin column so that a large volume of water can be treated. Nevertheless, the presence of the organic anions significantly increases the amount of iodine in aqueous solution and enhances the disinfecting power of that iodine.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an enhanced mixed source/capture for iodine treatment of water.

In treating water with iodine it has been usual to consider the process in terms of time versus temperature versus concentration. That is, a certain concentration of iodine must act for a certain amount of time at a given temperature to achieve adequate destruction of pathogens. Lowering any of the terms of this relationship results in less than optimum performance. With too low of an iodine concentration all of the pathogens cannot react with sufficient iodine within the given time. At too low of a temperature the reaction rate is too slow for disinfection to occur within the given time. Further, iodine is only slightly soluble in water so that if solid elemental iodine is used as a source, insufficient iodine may go into solution at a significantly below room temperature (25° C.).

Iodine is very soluble in some organic solvents and in an aqueous solution of potassium or sodium iodide (Lugol's solution). In addition certain organic compounds known as "iodophors" (iodine carriers) significantly enhance the solubility of iodine. The typical iodine source resin such as "MCV" resin (45% iodine by weight) from Umpqua Research or iodinated resin (A-605) from Purolite bind iodine fairly strongly so that they normally release considerably less iodine that pure iodine solid. Excess iodine and iodide are removed from the treated water by a "capture" resin such as "Iodosorb" from Umpqua Research or A-606 resin from Purolite.

Various additives could be used to enhance the release of iodine from these resins. It appears to be impractical to enhance the solubility and activity of iodine by adding organic solvents or typical iodophors to resins used for iodine treatment of water. The presence of organic solvents or iodophors in drinking water would be unacceptable. Of course, such additives could be removed with an activated carbon filter, but this would entail an additional component to the treatment system. Further, it would be necessary to constantly add these materials to the treatment stream—certainly an unfavorable departure from the self-contained nature of the resin-based treatment system. It should be possible to mobilize the iodine through the addition of sodium or potassium iodide, but this would require additional exchange resins to remove both the added iodide and the added cation.

In my earlier experiments on iodine disinfection I discovered that small organic acids—particularly citrate and isocitrate can be shown to enhance the disinfecting properties of iodine resin columns. The exact reason for this effect is not yet known. However, I have observed that citrate slowly reacts with and is very slowly reduced by iodine. There is considerable evidence that the most effective disinfecting compound is not actually iodine but rather an intermediate compound such as hypoiodous acid. Further, a number of my experiments suggested to me that citrate was somehow increasing the release of iodine from the resin. The reasons for this apparent enhanced iodine release may involve some interaction between the intermediate iodine compounds and elemental iodine—analogous to the interaction between iodide and elemental iodine which creates soluble tri-iodide in Lugol's solution. It may also be possible that citrate is a weak iodophor and directly enhances the solubility of iodine, or it may be that all of these factors and/or yet unknown factors are involved.

However, merely adding citrate to the water stream to be processed has many of the same drawbacks as adding iodide or iodophors. The goal is to enhance the resin system without making it more complex. I realized that many of the iodinated resins are actually ion exchange resins so it should be possible to replace whatever anion the resin carries (usually chloride) with citrate so that citrate would be present to enhance the iodine. While this approach definitely forms part of the present invention, I realized that it may be easier to replace the anion of the capture resin with citrate and then mix this modified resin with the iodine resin to create a mixed bed resin. In this way, citrate leaching off the capture resin would be available to enhance the solubility and reactivity of the iodine. Further, the capture resin could then serve to remove excess iodine and iodide. As iodine transfers to the citrated capture resin, that resin also begins to act as an enhanced iodine source. This process would continue until either the iodine or citrate becomes exhausted. This description is not intended to limit the present invention to the situation where only the capture resin is citrated. Both the iodine source resin and the capture resin can be citrated in a mixed bed arrangement. Or only the iodine source resin or only the capture resin can be citrated in a mixed bed arrangement. It is possible to used citrated source resin and/or citrated mixed bed resin with separate capture resin (not citrated) or entirely without capture resin. It is the use of resin to provide citrate and iodine together that is believed to make the current invention function. For example, a 1:1 mixture of iodine capture resin (such as Iodosorb from Umpqua or A-606 strong anion exchange resin from Purolite) and iodine source resin (such as Umpqua MCV or Purolite A-605) was placed into a 40 ml column and "citrated" by flowing through 100 ml of an approximately 10% (by weight) (actually, 96 g per liter) solution of tri-sodium citrate. About 2.5 column volumes of citrate solution appear to convert a majority of the exchange sites to citrate. It is likely that a greater volume of citrate would result in an even more complete conversion. The citrate solution exiting the column showed only about 49 g per liter of citrate using a citrate lyase-based spectrophotometric test for citrate.

The column was then washed with one liter (25 column volumes) of distilled water. Following the wash additional washing produced a column effluent with a concentration of 0.2 g citrate per liter. A similar concentration of citrate was released for at least 30 liters (750 column volumes). The citrated column was set up in parallel with an identical column that had not received the citrate treatment. It was found that test solutions of about $1\times10^6$ colony forming units of Escherichia coli per milliliter at a very high flow rate (approximately 2 liters per minute) resulted in total kill of the bacterial in the citrated column and only partial kill of the bacteria in the non-citrated column. The superior killing ability of the citrated column was intact even after the column had been washed with 30 liters of water.

The enhanced disinfection also extends to virus. EMC (encephalomyocarditis) virus was added to water. If the spiked water was tested directly on a cell culture, a viral endpoint assay indicated that the spiked water contained a viral titer of 5.3 logs in a first experiment and 5.1 logs of virus in a second experiment. When the virally spiked water was flowed through a normal 1:1 mixed resin column at approximately two liters per minute, there was no detectable kill of virus. However, when the samples were flowed through the citrated column at approximately two liters per minute, the results of the two experiments showed a viral titer of 4.3 (a one log reduction) and 3.6 (a reduction of 1.6 logs).

A third experiment was performed to test the effect of flow rate. Here the initial water had a viral titer of 5.4 log. When this material was flowed through a 40 ml 1:1 mixed bed column at either 2000 ml/min or 500 ml/min, there was no detectable killing of the virus. However, when this same material was flowed through a 40 ml 1:1 mixed bed column that was citrated, the 2000 ml/min sample showed a viral titer of 4.0 log (a reduction of 1.4 logs) while the 500 ml/min sample showed a viral titer of 1.8 log (a reduction of 3.6 logs).

In another experiment two 1:1 ratio iodinated resin to capture resin 40 ml columns were prepared. The first column was washed with 100 ml of 10% by weight tri-sodium citrate (pH 7.0). The solution was allowed to drain through by gravity and samples were taken for determination of iodine and iodide. The second column was washed with 100 ml of distilled water. The effluent from the water-washed column showed no detectable iodide and 1.0 ppm of iodine. Subsequent washes to the water-washed column showed no detectable iodide or iodine. However, washes of the citrated column showed iodide and iodine levels as listed in the following table. The listed wash volumes are cumulative so that "10 liters" indicates that approximately 10 liters had flowed through the column at that point.

| Wash | Iodide (ppm) | Iodine (ppm) |
| --- | --- | --- |
| 100 ml 10% citrate | 9.0 | 10.2 |
| 200 ml water | 1.0 | 3.8 |
| 1 liter | 0.9 | 4.0 |
| 2 liters | 1.0 | 3.5 |
| 3 liters | 1.0 | 3.7 |
| 4 liters | 0.8 | 3.8 |
| 5 liters | 1.1 | 3.8 |
| 6 liters | 1.0 | 3.9 |
| 7 liters | 0.9 | 4.1 |
| 8 liters | 0.7 | 4.0 |
| 9 liters | 0.9 | 3.6 |
| 10 liters | 1.2 | 3.9 |

The continued release of iodide indicates that citrate continues to slowly react with iodine. Most significantly, this reaction and/or the presence of citrate results in a dramatic continued release of iodine from the column—approximately 4 ppm whereas the level of iodine released from the control (non-citrated) column is not even detectable.

The continued enhanced iodine release translates directly into killing E. coli bacterial. One liter test suspensions ($1\times10^6$ cfu/ml) were prepared with tap water and poured onto the columns after the listed wash volume of water had already flowed through the column. The effluent from the columns was plated onto growth agar. The level of detected growth ranges from 1+ to 4+ (value of the starting test suspension) with "ng" indicating no detectable bacterial growth.

| Wash Volume | Citrated | Non-citrated |
| --- | --- | --- |
| 1 liter | ng | 3+ |
| 2 liters | ng | 3+ |
| 3 liters | ng | 2+ |
| 4 liters | ng | 3+ |
| 5 liters | ng | 2+ |
| 6 liters | ng | 3+ |
| 7 liters | ng | 2+ |
| 8 liters | ng | 2+ |
| 9 liters | ng | 2+ |

-continued

| Wash Volume | Citrated | Non-citrated |
|---|---|---|
| 10 liters | ng | 3+ |
| 20 liters | ng | 3+ |
| 30 liters | ng | 3+ |
| 40 liters | ng | 3+ |

These results indicate that the enhanced release of iodine caused by the citrate translates directly into enhanced killing of bacteria The above experiments were achieved by citrating a mixed bed of iodine source and iodine capture resins. To demonstrate that the citrate does not have to be added directly to the iodine source resin the capture resin was citrated before being mixed with the iodine source resin. Forty milliliters of 50% by weight tri-sodium citrate solution was prepared. Twenty milliliters of capture resin (Iodosorb) was added to the citrate solution and gently agitated for about six hours. Finally, the capture resin was separated from the citrate solution and mixed with an equal volume of iodine source resin (MCV) to create a 40 ml 1:1 citrated column. This column was washed with one column volume (40 ml) of water and the effluent showed 52 ppm of iodine. Washing was continued with 40 ml aliquots for five washes. The detected iodine concentration ranged between 50 and 60 ppm.

Replacing the typical anion on iodine source and capture resins with citrate results in a significantly higher level of iodine release from the iodine resin particularly in a mixed bed situation. This release can be sustained over a significant volume of water. The level of iodine release can be adjusted by altering the level of citation of the column as well as the ratio of source to capture resin. It would appear that citration of the capture resin might interfere with the ability of the resin to capture all of the iodine and iodide (alternatively, the greatly enhanced release of iodine and iodide may simply swamp the capture resin). Therefore, it may be desirable to insert a quantity of capture resin (non-citrated) downstream of the citrated resins to remove iodine and iodide from the treated water. Although trace amounts of citrate are not believed to be harmful, such a quantity of added capture resin would also remove any trace amounts of citrate in the treated water. It is believed that the much higher levels of iodine release achieved by the citrated resins will allow adequate disinfection without the prolonged holding times often required with iodine treatment of water. To the extent that "dwell" time with the iodine is still needed, this can be provided by separating the citrated resins from the final capture resin by a low line of sufficient length.

Although a major thrust of "treatment of water" is aimed towards treating water for human drinking, it is also contemplated that the present invention is also ideal for treating reclaimed or "gray" water from sewage treatment plants. Current levels of sewage treatment yield water that is perfectly usable except for the presence of human pathogens. As in the case of potable water these pathogens can be eliminated by chlorination or other treatment. The present iodine method is relatively immune to organic matter within the treated sewage and produces a treated water essentially free of any undesirable additives.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A device for flow treatment of water to destroy pathogens therein comprising a first bed of an anion exchange resin in which at least 20% of the anion exchange sites bind an anion of an organic acid selected from the group consisting of citric acid and isocitric acid and a source of elemental iodine, wherein the source of elemental iodine comprises a resin containing chemically free iodine and iodine is released in an amount sufficient ot destroy pathogens in said water.

2. The device of claim 1, wherein the resin containing chemically free iodine is an anion exchange resin in which at least 20% of the anion exchange sites bind an anion of an organic acid selected from the group consisting of citric acid and isocitric acid.

3. The device of claim 1 further comprising a second bed of anion exchange resin disposed downstream of the source of elemental iodine.

4. The device of claim 1, wherein the first bed of anion exchange resin and the source of elemental iodine are mixed together.

5. A device for flow treatment of water to destroy pathogens therein comprising a mixed bed of an anion exchange resin in which at least 20% of the anion exchange sites bind a citrate anion or an isocitrate anion and a source of elemental iodine, wherein the source of elemental iodine comprises a resin containing chemically free iodine and iodine is released in an amount sufficient to destroy pathogens in said water.

6. The device of claim 5, wherein the resin containing chemically free iodine is an anion exchange resin in which at least 20% of the anion exchange sites bind a citrate or an isocitrate anion.

7. The device of claim 5 further comprising a second bed of anion exchange resin disposed downstream of the source of elemental iodine.

8. A method for flow treatment of water to destroy pathogens therein comprising the steps of contacting water with an anion exchange resin in which at least 20% of the anion exchange sites bind an anion of an organic acid selected from the group consisting of citric acid and isocitric acid and contacting water with a source of elemental iodine, wherein the source of elemental iodine comprises a resin containing chemically free iodine and iodine is released in an amount sufficient ot destroy pathogens in said water.

9. The method of claim 8, wherein the resin containing chemically free iodine is an anion exchange resin in which at least 20% of the anion exchange sites bind an anion of an organic acid selected from the group consisting of citric acid and isocitric acid.

10. The method of claim 8, wherein the steps of contacting the anion exchange resin and the step of contacting the source of elemental iodine are carried out simultaneously.

11. The method of claim 8 further comprising the step of contacting water with anion exchange resin disposed downstream of the source of elemental iodine.

12. A device for flow treatment of water to destroy pathogens therein comprising a first bed of an anion exchange resin which has anion exchange sites binding anions of an organic acid selected from the group consisting of citric acid and isocitric acid and a source of elemental iodine, wherein the organic acid is present in an amount effective to enhance release of the iodine, the source of elemental iodine comprises a resin containing chemically free iodine and iodine is released in an amount sufficient to destroy pathogens in said water.

13. The device of claim 12, wherein the resin containing chemically free iodine is an anion exchange resin which has anion exchange sites binding anions of an organic acid selected from the group consisting of citric acid and isocitric acid, and wherein the organic acid is present in an amount effective to enhance release of the iodine.

14. The device of claim 12 further comprising a second bed of anion exchange resin disposed downstream of the source of elemental iodine.

15. The device of claim 12, wherein the first bed of anion exchange resin and the source of elemental iodine are mixed together.

16. A device for flow treatment of water to destroy pathogens therein comprising a mixed bed having a first bed of resin with anion exchange sites binding citrate or isocitrate anions and a source of elemental iodine, wherein the organic acid is present in an amount effective to enhance release of the iodine, the source of elemental iodine comprises a resin containing chemically free iodine and iodine is released in an amount sufficient to destroy pathogens in said water.

17. The device of claim 16, wherein the resin containing chemically free iodine is a resin having anion exchange sites binding citrate anions or isocitrate anions.

18. The device of claim 16 further comprising a second bed of anion exchange resin disposed downstream of the source of elemental iodine.

19. A method for flow treatment of water to destroy pathogens therein comprising the steps of contacting water with an anion exchange resin having anion exchange sites binding anions of an organic acid selected from the group consisting of citric acid and isocitric acid and contacting water with a source of elemental iodine, wherein the organic acid is present in an amount effective to enhance release of the iodine, the source of elemental iodine comprises a resin containing chemically free iodine and iodine is released in an amount sufficient to destroy pathogens in said water.

20. The method of claim 19, wherein the resin containing chemically free iodine is an anion exchange resin having anion exchange sites bind anions of an organic acid selected from the group consisting of citric acid and isocitric acid, and wherein the organic acid is present in an amount effective to enhance release of the iodine.

21. The method of claim 19, wherein the steps of contacting the anion exchange resin and the step of contacting the source of elemental iodine are carried out simultaneously.

22. The method of claim 19 further comprising the step of contacting water with anion exchange resin disposed downstream of the source of elemental iodine.

* * * * *